United States Patent [19]
Tanamal et al.

[11] Patent Number: 5,755,811
[45] Date of Patent: May 26, 1998

[54] PROSTHETIC IMPLANT WITH FINS

[75] Inventors: Linggawati Tanamal, Warsaw, Ind.; Roberto Giacometti, Milan; Paolo Cherubino, Varese, both of Italy

[73] Assignee: Zimmer, Inc., Warsaw, Ind.

[21] Appl. No.: 825,845

[22] Filed: Apr. 4, 1997

Related U.S. Application Data

[63] Continuation of Ser. No. 519,213, Aug. 25, 1995, abandoned.
[51] Int. Cl.⁶ .................................................. A61F 2/36
[52] U.S. Cl. .................................................. 623/23
[58] Field of Search .............................. 623/19, 23, 22, 623/18; 606/62, 67, 95

[56] References Cited

U.S. PATENT DOCUMENTS

| | | |
|---|---|---|
| Re. 28,895 | 7/1976 | Noiles . |
| 2,719,522 | 10/1955 | Hudack ........................ 128/92 |
| 3,466,670 | 9/1969 | Christiansen . |
| 3,658,056 | 4/1972 | Huggler et al. . |
| 3,685,058 | 8/1972 | Tronzo . |
| 3,874,003 | 4/1975 | Moser et al. . |
| 3,905,777 | 9/1975 | Lacroix ........................ 29/183.5 |
| 3,918,441 | 11/1975 | Getscher ...................... 623/23 X |
| 3,996,625 | 12/1976 | Noiles . |
| 4,021,865 | 5/1977 | Charnley . |
| 4,287,617 | 9/1981 | Tornier . |
| 4,404,693 | 9/1983 | Zweymüller . |
| 4,430,761 | 2/1984 | Niederer et al. . |
| 4,532,661 | 8/1985 | Helpern ........................ 623/23 |
| 4,546,501 | 10/1985 | Gustilo et al. ................ 623/23 |
| 4,549,319 | 10/1985 | Meyer .......................... 623/22 |
| 4,608,053 | 8/1986 | Keller ........................... 623/23 |
| 4,623,349 | 11/1986 | Lord ............................. 623/18 |
| 4,645,506 | 2/1987 | Link ............................. 623/23 |
| 4,661,112 | 4/1987 | Müller .......................... 623/22 |
| 4,664,668 | 5/1987 | Beck et al. ................... 623/23 |
| 4,678,471 | 7/1987 | Noble et al. ................. 623/16 |

(List continued on next page.)

FOREIGN PATENT DOCUMENTS

| | | |
|---|---|---|
| 0 112 435A1 | 7/1984 | European Pat. Off. . |
| 0 145 938B1 | 6/1985 | European Pat. Off. . |
| 0 145 939A2 | 6/1985 | European Pat. Off. . |
| 0 159 462B1 | 10/1985 | European Pat. Off. . |
| 0 169 976B1 | 2/1986 | European Pat. Off. . |
| 0 187 903A1 | 7/1986 | European Pat. Off. . |
| 0 222 236A1 | 5/1987 | European Pat. Off. . |
| 0 238 860A2 | 9/1987 | European Pat. Off. . |
| 0 240 815A1 | 10/1987 | European Pat. Off. . |
| 366945 | 5/1990 | European Pat. Off. ......... 623/23 |
| 0 393 608A2 | 10/1990 | European Pat. Off. . |
| 0 405 618A1 | 1/1991 | European Pat. Off. . |
| 0 494 040A2 | 7/1992 | European Pat. Off. . |
| 0 499 480A1 | 8/1992 | European Pat. Off. . |
| 948690 | 1/1949 | France ........................... 606/67 |
| 2 528 307A | 12/1983 | France . |
| 2589353 | 5/1987 | France ........................... 623/22 |
| 2 639 821 | 6/1990 | France . |
| 2627569 | 12/1977 | Germany ....................... 623/23 |
| 459962 | 5/1966 | Switzerland . |
| 571255 | 9/1977 | U.S.S.R. ........................ 606/67 |
| 1 292 561 | 10/1972 | United Kingdom . |
| 2 118 043 | 10/1983 | United Kingdom . |
| 2 197 204 | 5/1988 | United Kingdom . |

OTHER PUBLICATIONS

Smith & Nephew Richards, Inc.—"The Bio–Fit™ Stem"—No date available.

Smith & Nephew Richards, Inc.—"The Ti–Fit™ System"—No date available.

Smith & Nephew Richards, Inc.—"The Master Series™ Stems & Cups"—No date available.

Primary Examiner—David H. Willse
Attorney, Agent, or Firm—Margaret L. Geringer

[57] ABSTRACT

The present invention provides a prosthetic implant 1 which includes a stem 2 having two lateral fins 20. The lateral fins 20 extend outwardly from the lateral side 6 of the stem 2, such that the lateral face 21 of each fin 20 is flush with the lateral side 6 of stem 2.

20 Claims, 2 Drawing Sheets

U.S. PATENT DOCUMENTS

| | | | |
|---|---|---|---|
| 4,698,063 | 10/1987 | Link et al. | 623/23 |
| 4,704,128 | 11/1987 | Frey | 623/23 |
| 4,728,334 | 3/1988 | Spotorno | 623/23 |
| 4,770,659 | 9/1988 | Kendall | 623/22 |
| 4,770,661 | 9/1988 | Oh | 623/23 |
| 4,784,124 | 11/1988 | Kaltenbrunner et al. | |
| 4,795,471 | 1/1989 | Oh | 623/23 |
| 4,904,269 | 2/1990 | Elloy et al. | 623/23 |
| 4,938,773 | 7/1990 | Strand | 623/23 |
| 4,944,761 | 7/1990 | Stuhmer et al. | 623/23 |
| 4,946,379 | 8/1990 | Berchem | 623/18 |
| 4,978,357 | 12/1990 | Goymann et al. | 623/18 |
| 5,108,453 | 4/1992 | Kotz et al. | 623/23 |
| 5,116,377 | 5/1992 | Skripitz et al. | 623/23 |
| 5,201,767 | 4/1993 | Caldarise et al. | 623/18 |
| 5,258,035 | 11/1993 | Hofmann et al. | 623/23 |

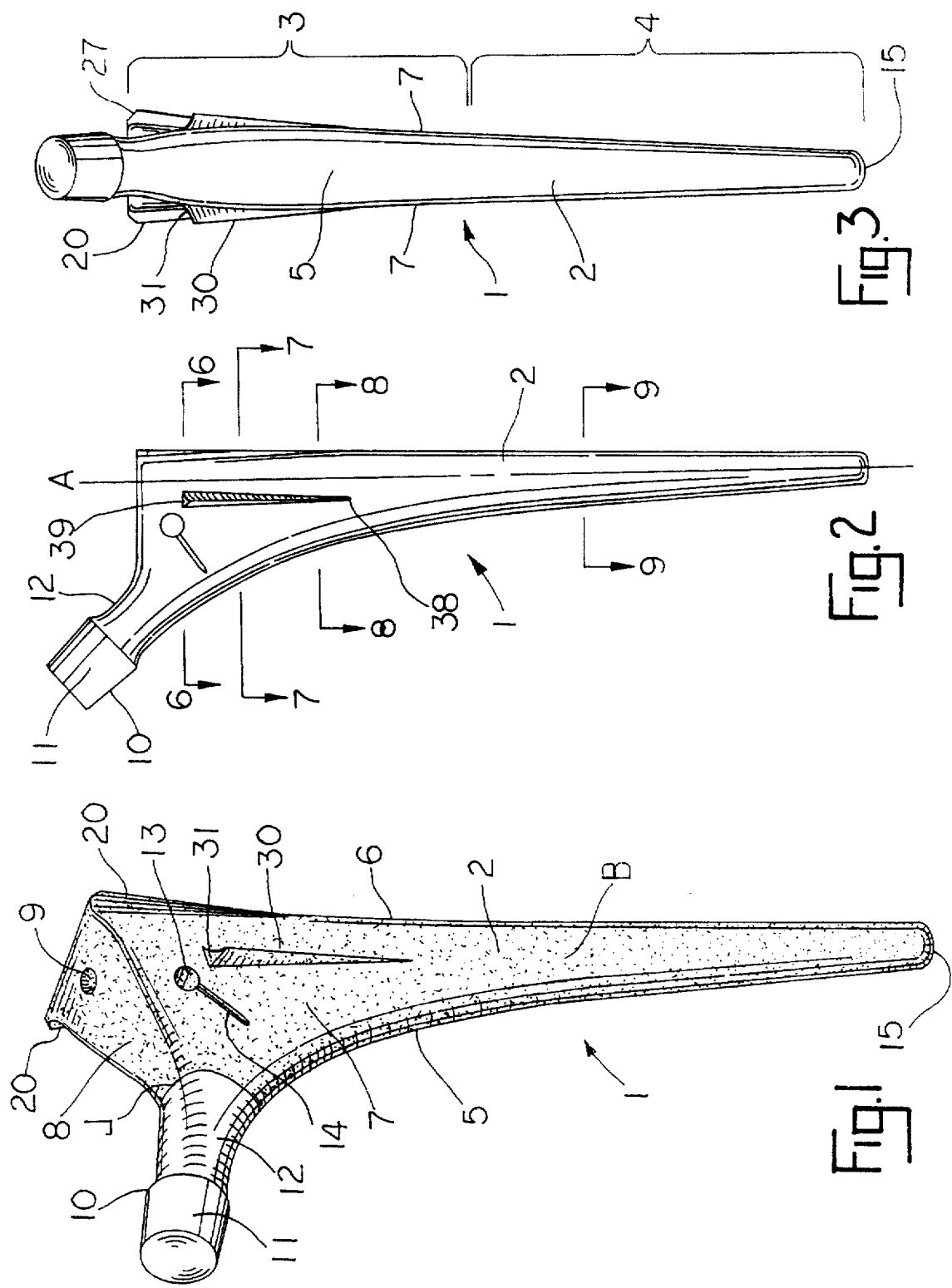

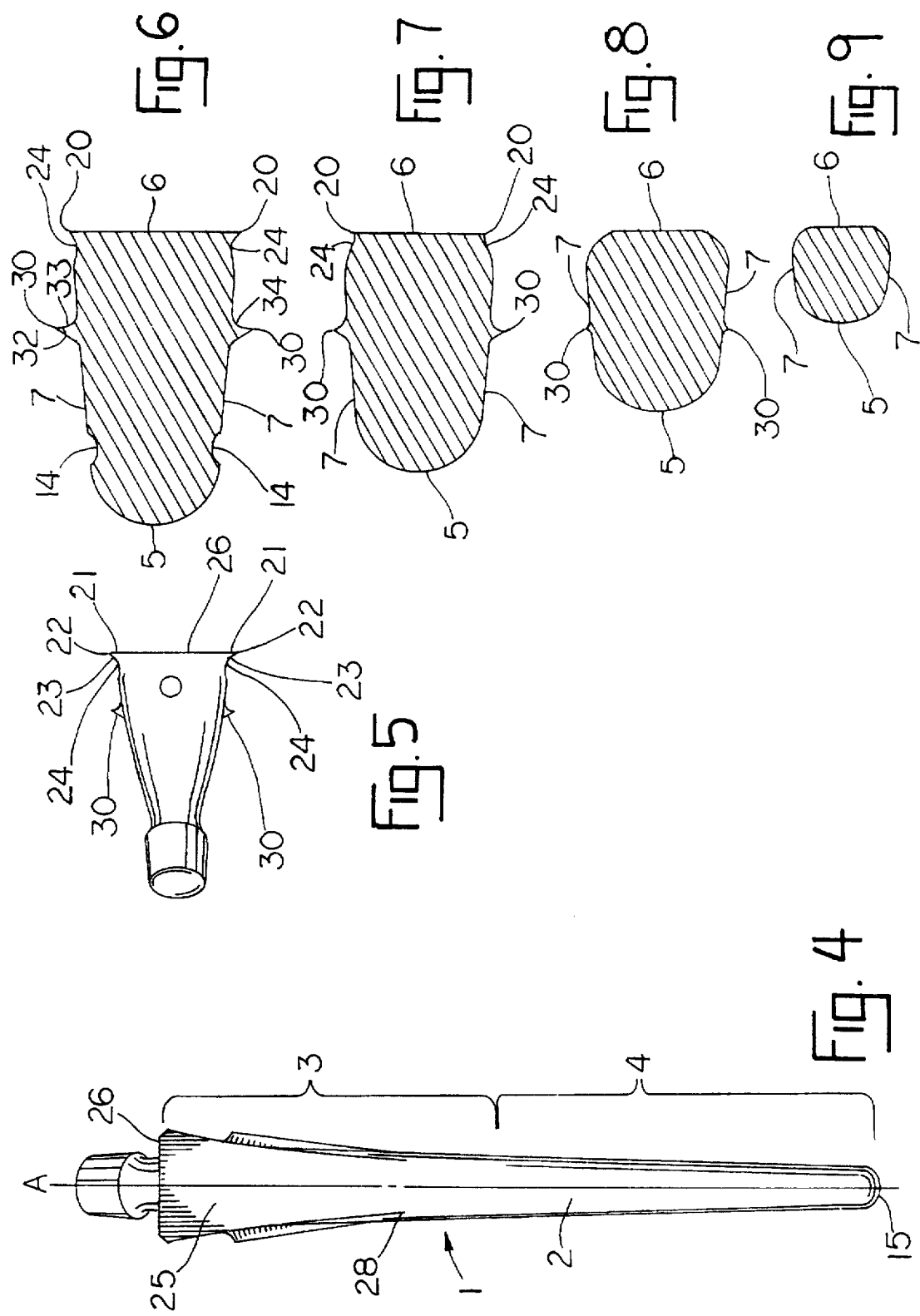

PROSTHETIC IMPLANT WITH FINS

This application is a continuation of application Ser. No. 08/519,213 filed Aug. 25, 1995, now abandoned.

FIELD OF THE INVENTION

The present invention relates to a prosthetic implant, and more particularly to a stemmed implant having fins extending therefrom.

BACKGROUND OF THE INVENTION

It is known in the field of orthopaedics to utilize fins which extend from a stem portion of a prosthetic implant. The following patents disclose fins along the anterior and posterior sides of femoral implants in which the fins are inset from the lateral side of the stem: U.S. Pat. No. 4,944,761 to Stuhmer et al; U.S. Pat. No. 4,795,471 to Oh; U.S. Pat. No. 4,728,334 to Spotorno; U.S. Pat. No. 4,704,128 to Frey; U.S. Pat. No. 4,698,063 to Link et al. and French Patent 2,639,821 to Istria. U.S. Pat. Nos. 4,944,761 and 4,698,063 also include fins projecting from the lateral side. Also, U.S. Pat. No. 5,201,767 to Caldarise et al. discloses a plurality of fins extending about the proximal lateral side of the femoral stem, and U.S. Pat. No. 4,549,319 to Meyer discloses a plurality of fins extending circumferentially about the femoral stem.

SUMMARY OF THE INVENTION

The present invention provides a prosthetic implant which includes a stem having two lateral fins. The lateral fins extend outwardly from the lateral side of the stem, such that the lateral face of each fin is flush with the lateral side of the stem. The lateral face of each of the lateral fins forms a substantially planar, triangular surface with the lateral side of the stem. The triangular surface is formed by the outer edges of the two lateral fins and the lateral edge of the shoulder of the implant. The lateral fins extend from the proximal portion of the stem.

The stem further includes a secondary fin extending from each sidewall. Each secondary fin is inset from the lateral side of the stem toward the medial side. The secondary fins are substantially triangular in cross-section, and extend from the proximal portion of the stem. The secondary fins include a top surface spaced below the shoulder of the stem, will lateralize the prosthesis to achieve a valgus position in the bone.

Another advantage of the invention is to provide secondary stability to the shaped stem of the implant.

A further object of the invention is to provide rotational stability of the stem in the bone.

Still other advantages of the invention will become apparent upon reference to the accompanying drawings.

BRIEF DESCRIPTION OF THE DRAWINGS

FIG. 1 is a perspective view of a hip prosthesis according to the present invention.

FIG. 2 is a side view of the hip prosthesis of FIG. 1.

FIG. 3 is a front view thereof.

FIG. 4 is a rear view thereof.

FIG. 5 is a top plan view thereof.

FIG. 6 is a cross-sectional view of the prosthesis taken along lines 6—6 of FIG. 2.

FIG. 7 is a cross-sectional view of the prosthesis taken along lines 7—7 of FIG. 2.

FIG. 8 is a cross-sectional view of the prosthesis taken along lines 8—8 of FIG. 2.

FIG. 9 is a cross-sectional view of the prosthesis taken along lines 9—9 of FIG. 2.

DESCRIPTION OF THE PREFERRED EMBODIMENT

FIGS. 1–9 illustrate a particularly advantageous embodiment of a prosthetic implant 1 according to the present invention. The invention will be described with reference to a femoral component of a hip prosthesis, and is particularly suitable as such. However, it is understood that the principles of the invention may be suitable for other implants having elongated fixation stems, such as a humeral component for a shoulder prosthesis.

The femoral component or prosthetic implant 1 includes a stem 2 having a proximal portion 3 and a distal portion 4. The stem also includes a medial side 5 and a lateral side 6 separated by a pair of sidewalls 7. Sidewalls 7 correspond to the anterior and posterior sides of the femoral component 1. The proximal portion 3 of the stem 2 terminates proximally in a superior shoulder 8 with a neck 10 extending therefrom. The stem 2 includes two lateral fins 20 extending outwardly from the lateral side 6. The lateral fins 20 each include a lateral face 21 which is flush with the lateral side 6 of the stem 2.

The lateral fins 20 each have an outer edge 22 such that a width is defined between the two outer edges 22 of fins 20. This width increases as the fins 20 extend toward shoulder 8. The lateral face 21 of each of the lateral fins forms a substantially planar, triangular surface 25 which blends into the lateral side 6 of stem 2.

The lateral side 6 is a substantially flat, planar surface which extends from the shoulder 8 to distal tip 15 of stem 2. This planar surface is substantially parallel to the longitudinal axis A of stem 2. Thus, the lateral side 6 is essentially a flat planar surface with a 0° angle relative to axis A of stem 2.

The lateral fins 20 extend from the proximal portion 3 of stem 2. When the femoral component is positioned in a femur (not shown), the position of the distal end 28 of fins 20 corresponds approximately to the junction between the metaphysis and diaphysis or the isthmus junction of the femur. The fins 20 extend proximally from distal end 28 to the superior shoulder 8. The triangular surface is formed by the outer edges 22 of the two lateral fins and by a lateral edge 26 of shoulder 8. A chamfer 27 may be provided between outer edges 22 and the lateral edge 26 of shoulder 8 to prevent a sharp corner on fins 20. The lateral fins are positive cutting or self cutting fins, such that upon insertion of the femoral component 1 into the femur, the fins 20 will cut into and become embedded in the cancellous bone of the femur. The outer edge 22 of fins 20 form a concave curve for better fitting of the fin in the femoral canal. The planar triangular surface 25 is a continuation of the straight planar lateral side 6. The curved outer edges 22 of fins 20 blend into the lateral side of stem 2.

The lateral fins 20 include an inner face 23 which is comprised of a concave groove 24 which extends from the outer edge 22 of each fin 20 toward a respective one of the sidewalls 7 to blend the lateral fins 20 into the respective sidewall 7. The groove 24 provides a means of releasing stress while compressing the bone when the component 1 is implanted in a femur.

With the guidance of the straight lateral side 6, the lateral fins 20 on the proximal portion 3 of stem 2 will lateralize the femoral component 1 to achieve a valgus position in the femur. The straight lateral side 6 along with the lateral fins 20 which expand or widen as the fins 20 approach shoulder 8 help to provide rotational stability for the stem 2 in the femur to supplement the fixation of the stem in the femur. The fins 20 also provide a secondary stability to the wedge shaped body of stem 2. The wedge shape of the stem 2 provides the primary mode of fixation, while the fins 20 provide secondary fixation by providing rotational stability.

The stem 2 has a cross-section which is substantially wedge-shaped such that the sidewalls 7 angle toward each other as the sidewalls approach medial side 5. The medial side 5 of the cross-section comprises a convex curve. In addition, the sidewalls 7 are substantially planar and taper toward the longitudinal axis A of stem 2 as the sidewalls progress from the shoulder 8 toward the distal tip 15 of stem 2. The proximal portion 3 of the medial side 5 of stem 2 is comprised of a concave curve which blends into the distal portion 4 of the medial side 5 which tapers toward the longitudinal axis A as the medial side 5 extends toward the distal tip 15 of stem 2. The taper of the medial side of the distal portion 4 enhances proximal fixation in the femur.

The femoral component 1 further includes a secondary fin 30 extending from each sidewall 7. Each secondary fin 30 is inset about 7 to 14 mm from the lateral side 6 toward the medial side 5. Fins 30 extend from the proximal portion 3 of stem 2. When the femoral component 1 is positioned in a femur, the position of the distal end 38 of fins 30 also corresponds approximately to the isthmus junction of the femur. The fins 30 stop at a proximal end 39 at about the level of the lesser trochanter of the femur in order to help prevent the femur from splitting upon insertion of the femoral component 1 into the femur. Fins 30 provide additional rotational stability. The fins 30 include a top surface 31 which is spaced about 14 to 19 mm below the shoulder 8 of stem 2. The length of the fins 30 is about 27–39 mm. The top surface 31 is chamfered downwardly toward distal tip 15 of stem 2. The chamfer of top surface 31 is preferably formed by a concave radius and is incorporated onto fins 30 for ease of removal in case the femoral component 1 must be removed, such as for revision surgery.

The fins 30 are substantially triangular in cross-section. The secondary fins 30 each have a lateral facing surface 33 which extends substantially perpendicular to the corresponding sidewall 7 of stem 2. A radius 34 helps to blend the lateral facing surface 33 to sidewall 7 while providing a compression surface for the bone when component 1 is implanted in a femur. The medial facing surface 32 forms an acute angle, such as about 35°, with lateral facing surface 33. The secondary fins 30 extend further away from stem 2 as fins 30 progress toward shoulder 8.

Both the lateral fins 20 and the secondary fins 30 extend in a longitudinal direction relative to stem 2. Fins 20 and fins 30 all extend proud from the stem 2. Fins 20 and 30 may extend up to about 2.5mm proud of the stem 2, and may be up to about 2 to 3 mm wide. This femoral component 1 of the present invention is generally intended for use in a press-fit noncemented application. Thus, the shape of the corresponding rasp (not shown) which prepares the bone opening to receive the femoral component 1, corresponds to the shape of the stem 2. However, the corresponding rasp preferably does not include fins, so that when the actual femoral component 1 is implanted into the bone, the stem 2 will form a press-fit with the opening prepared by the rasp, while the fins 20 and 30 cut into the bone and become embedded into the cancellous bone of the femur.

It is noted that the femoral component 1 may be made with a separate modular head (not shown) which is fitted to tapered neck 10, or the head may be integrally formed on the prosthetic implant 1, as desired. The neck 10, as shown, for fitting with various styles and sizes of modular heads includes a first taper 11 which is sized to frictionally fit with a corresponding recess (not shown) in a modular head. The taper 11 thus mates with this recess. The neck 10 includes a reduced neck portion 12 which extends outwardly of the modular head in order to provide for a better range of motion of the femoral component 1 with a corresponding acetabular component (not shown). Such a reduced neck is well known in the art of orthopaedics. The present invention preferably utilizes a 12/14 taper on taper 11 to mate with a corresponding 12/14 tapered recess of a corresponding femoral head. The reduced neck portion 12 is then a 10/12 taper to provide for the better range of motion. The femoral component 1 also preferably comes in a range of sizes, such as 9,10,11,12,13, 14,15,16,17,18, and 19 mm length stems. However, it is noted that the present invention is not limited to the particular sizes noted herein.

The femoral component 1 may also include a recess 9, as is known in the art, for use with a stem inserter for assisting in positioning the component 1 in the femur. A proximal through hole may also be provided, as is known in the art, for use with an extraction rod in case the component 1 needs to be removed from the bone. A groove 14 is provided which corresponds to the osteotomy level on the femur. The groove 14 helps to properly position the component 1 in the bone.

The femoral component 1 also may include a roughened surface finish, such as a blast finish to enhance the fixation of component 1 to the bone. A roughened surface, such as a corundum blast surface, or any other suitable roughened surface may be utilized. This blast surface provides an ongrowth surface which may enable bone to grow onto the surface of the stem 2 to enhance long term fixation. The blast surface B, as shown in FIG. 1, may be provided from approximately the junction J of the stem 2 with the neck 10 to the distal tip 15. The component 1 is preferably made of a titanium alloy; however, any suitable material may be utilized. The component may be manufactured by any suitable manufacturing methods.

While this invention has been described in terms of a particularly advantageous embodiment, those skilled in the art can appreciate that modifications can be made without departing from the spirit and scope of this invention.

We claim:

1. A prosthetic implant including an elongated stem having a longitudinal axis and a proximal portion and a distal portion, and a medial side and an oppositely located lateral side separated by a pair of spaced apart sidewalls forming a substantially solid stem adapted for insertion in a prepared opening in a bone, and wherein the proximal portion of the stem terminates proximally in a superior shoulder with a neck extending medially and superiorly therefrom, the stem includes two lateral fins extending outwardly from the lateral side, the lateral fins each include a lateral face which is flush with the lateral side of the stem, and wherein the lateral face of each of the lateral fins forms a substantially planar surface with the lateral side of the stem, and wherein said substantially planar surface is substantially parallel to the longitudinal axis of the stem and wherein the substantially planar surface formed by the lateral face of each of the lateral fins and the lateral side of the stem is a substantially planar, triangular surface.

2. The implant of claim 1 wherein the two lateral fins each have an outer edge, and wherein a width is defined between the two outer edges of the fins, said width increasing as the fins extend toward the shoulder.

3. The implant of claim 1 wherein the lateral fins extend from the proximal portion of the stem.

4. The implant of claim 1 wherein the lateral fins are self cutting fins.

5. The implant of claim 1 wherein the two lateral fins each have an outer edge and wherein each outer edge forms a concave curve.

6. The implant of claim 1 wherein the two lateral fins each have an outer edge and wherein the triangular surface is formed by the outer edges of the two lateral fins and a lateral edge of the shoulder.

7. The implant of claim 6 wherein each outer edge forms a concave curve.

8. The implant of claim 1 wherein the stem has a cross-section which is substantially wedge-shaped such that the sidewalls angle toward each other as the sidewalls approach the medial side.

9. The implant of claim 8 wherein the medial side of the cross-section comprises a convex curve.

10. The implant of claim 1 wherein the sidewalls are substantially planar and taper toward the axis as the sidewalls progress from the shoulder toward a distal tip of the stem.

11. The implant of claim 1 wherein the lateral side is a substantially flat, planar surface which extends from the shoulder to a distal tip of the stem and which planar surface is substantially parallel to the axis of the stem.

12. The implant of claim 1 wherein the proximal portion of the medial side of the stem is comprised of a concave curve which blends into the distal portion of the medial side which distal portion tapers toward the axis as the medial side extends toward a distal tip of the stem.

13. The implant of claim 1 wherein the lateral fins include an inner face which is comprised of a concave groove which extends from an outer edge of each fin toward a respective one of the sidewalls to blend the lateral fins into the respective sidewall.

14. The implant of claim 1 wherein the stem further includes a secondary fin extending from each sidewall, each said secondary fin being inset from the lateral side toward the medial side.

15. The implant of claim 14 wherein the secondary fins are substantially triangular in cross-section and extend from the proximal portion of the stem, and wherein the secondary fins include a top surface spaced below the shoulder of the stem.

16. The implant of claim 15 wherein the top surface of the secondary fin is chamfered downwardly toward a distal tip of the stem.

17. The implant of claim 14 wherein the lateral fins and the secondary fins extend in a longitudinal direction relative to the stem.

18. The implant of claim 14 wherein the secondary fins extend a further distance away from the stem as the secondary fins progress toward the shoulder.

19. The implant of claim 14 wherein the secondary fins each have a lateral facing surface which extends substantially perpendicular to the corresponding sidewall of the stem and is blended to the stem by a radius, and a medial facing surface which forms an acute angle with the lateral facing surface.

20. The implant of claim 1 wherein the implant is a femoral component of a prosthetic hip joint.

* * * * *